(12) United States Patent
Frank et al.

(10) Patent No.: US 11,558,512 B2
(45) Date of Patent: *Jan. 17, 2023

(54) AUTOMATED SYSTEM AND METHOD FOR ELECTRONIC HEALTH RECORD INDEXING

(71) Applicant: Document Imaging Systems Corp., Fenton, MO (US)

(72) Inventors: Kevin C. Frank, High Ridge, MO (US); Patrick J. Karpen, Webster Groves, MO (US)

(73) Assignee: Document Imaging Systems Corp., Kirkwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/482,159

(22) Filed: Sep. 22, 2021

(65) Prior Publication Data
US 2022/0013204 A1 Jan. 13, 2022

Related U.S. Application Data

(63) Continuation of application No. 16/885,756, filed on May 28, 2020, now Pat. No. 11,158,409, which is a
(Continued)

(51) Int. Cl.
*H04N 1/00* (2006.01)
*G06Q 10/10* (2012.01)
(Continued)

(52) U.S. Cl.
CPC ......... *H04N 1/00236* (2013.01); *G06F 16/22* (2019.01); *G06F 16/285* (2019.01);
(Continued)

(58) Field of Classification Search
CPC ........ G06F 16/22; G06F 16/285; G06F 16/93; G06Q 10/10; G16H 10/60; G16H 15/00;
(Continued)

(56) References Cited

U.S. PATENT DOCUMENTS

2002/0194026 A1* 12/2002 Klein ................. G06Q 10/10
705/2
2003/0160095 A1* 8/2003 Segal ................. G16H 10/60
235/375
(Continued)

OTHER PUBLICATIONS

A. M. Alghoson, "Medical Document Classification Based on MeSH," 2014 47th Hawaii International Conference on System Sciences, 2014, pp. 2571-2575, doi: 10.1109/HICSS.2014.324. (Year: 2014).*
(Continued)

*Primary Examiner* — Joy Chng
(74) *Attorney, Agent, or Firm* — Fresh IP PLC; John R. Bednarz

(57) ABSTRACT

A system includes one or more processors to receive a representation of a document from a client computing device, the document comprising one of a scanned document, a faxed document, and an electronic document, determine a document type of the document based at least on the representation of the document, index the document using a classification and index processing engine based on the document type, the document type comprising at least one of a plurality of document types used by an electronic health record (EHR) system, extract index data from the document based on the document type using the classification and index processing engine, and match the document with a patient from a database of the EHR system using the index data when the classification and index processing engine successfully indexes the document and extracts index data from the document.

20 Claims, 10 Drawing Sheets

Related U.S. Application Data continuation of application No. 15/938,738, filed on Mar. 28, 2018, now Pat. No. 10,706,960, which is a continuation of application No. 14/536,409, filed on Nov. 7, 2014, now Pat. No. 9,959,584.

(60) Provisional application No. 61/901,933, filed on Nov. 8, 2013.

(51) Int. Cl.
| | | |
|---|---|---|
| *G16H 15/00* | (2018.01) | |
| *G16H 10/60* | (2018.01) | |
| *G06F 16/22* | (2019.01) | |
| *G06F 16/28* | (2019.01) | |
| *G06F 16/93* | (2019.01) | |

(52) U.S. Cl.
CPC ............ *G06F 16/93* (2019.01); *G06Q 10/10* (2013.01); *G16H 10/60* (2018.01); *G16H 15/00* (2018.01); *H04N 1/00209* (2013.01); *H04N 1/00244* (2013.01); *H04N 2201/0079* (2013.01); *H04N 2201/0081* (2013.01); *H04N 2201/0093* (2013.01)

(58) Field of Classification Search
CPC ........... H04N 1/00209; H04N 1/00236; H04N 1/00244; H04N 2201/0079; H04N 2201/0081; H04N 2201/0093
USPC ........................................................ 705/2–3
See application file for complete search history.

(56) References Cited

U.S. PATENT DOCUMENTS

| | | | | |
|---|---|---|---|---|
| 2005/0120120 | A1* | 6/2005 | Suzuki .................. | G06F 3/1203 709/229 |
| 2007/0013967 | A1* | 1/2007 | Ebaugh ................ | G06V 30/418 707/E17.084 |

OTHER PUBLICATIONS

F. Esposito, S. Ferilli, T. M. A. Basile and N. Di Mauro, "Automatic content-based indexing of digital documents through intelligent processing techniques," Second International Conference on Document Image Analysis for Libraries (DIAL'06), 2006, pp. 16-219, doi: 10.1109/DIAL.2006.5. (Year: 2006).*

Non-Final Office Action dated Jun. 29, 2017, issued in U.S. Appl. No. 14/536,409; 20 pages.

Notice of Allowance and Fees Due, dated Jan. 19, 2018, issued in U.S. Appl. No. 14/536,409; 10 pages.

Non-Final Office Action dated Jan. 7, 2020, issued in U.S. Appl. No. 15/938,738; 17 pages.

Notice of Allowance and Fees Due, dated Apr. 29, 2020, issued in U.S. Appl. No. 15/938,738; 10 pages.

Non-Final Office Action dated Aug. 3, 2021, issued in U.S. Appl. No. 16/885,756; 5pages.

Notice of Allowance and Fees Due, dated Sep. 13, 2021, issued in U.S. Appl. No. 16/885,756; 8 pages.

* cited by examiner

FIG. 7

Attn: Dr. Jane Smith
Subject: Radiology Report
Patient Name: John Patient
Registration Number: 100330031

Date of Birth: Jun 14, 2008
Hospital Visit Date: Aug 29, 2014

Ordering Physician: Dr. Jane Smith

AUTOMATED SYSTEM AND METHOD FOR ELECTRONIC HEALTH RECORD INDEXING

CROSS-REFERENCE TO RELATED APPLICATIONS

This application is a continuation of U.S. application Ser. No. 16/885,756, entitled "Automated System and Method for Electronic Health Record Indexing," filed May 28, 2020, which claims priority to U.S. application Ser. No. 15/938,738, entitled "Automated System and Method for Electronic Health Record Indexing," filed Mar. 28, 2018, which claims priority to U.S. application Ser. No. 14/536,409, entitled "Automated System and Method for Electronic Health Record Indexing," filed Nov. 7, 2014, which claims priority to U.S. Application No. 61/901,933 entitled "Automated System and Method for Electronic Health Record Indexing," filed Nov. 8, 2013, the disclosures of which are hereby incorporated herein by reference.

FIELD

The present disclosure relates generally to systems and methods for electronic health record indexing. More particularly, systems and methods provide a web-based interface for importing physical and/or electronic documents, automatically indexing the documents by document type, patient, and other relevant data, and transmitting representations of the documents to an electronic health record (EHR) system.

BACKGROUND

Due to government regulations, healthcare facilities have had to transition from paper-based systems and hybrid paper/electronic systems to fully electronic systems. Electronic Health Record (EHR) systems collect and organize digitally formatted electronic health information and documents for patients in a healthcare facility or organization. EHR systems are designed to provide a paperless environment and better access to documents and data, but oftentimes importing documents and data is difficult and tedious.

Importing and processing hundreds and even thousands of documents on a daily basis into an EHR system is a challenging and inefficient task. Clinical data can be delivered to an EHR system inaccurately and inconsistently which can negatively affect patients, doctors, and staff at a healthcare facility. As an example, documents and data may be matched with an incorrect patient and/or documents and data may be classified incorrectly. These errors can be caused by healthcare employees who are working very quickly, often by necessity, to import documents and data. These problems may cause a healthcare facility and its employees to be less efficient and can be very costly.

Conventional EHR systems do not provide interfaces that allow a user to import physical and/or electronic documents and automatically index the documents by document type, patient, and other relevant data. This makes importing documents and data into an EHR system overly complicated and prone to error.

SUMMARY

According to one aspect, a system is provided for automated electronic health record indexing documents and data. The system provides a client computing device with a web-based interface to interact with document classification and indexing services. The system includes at least one client computing device having a processor to receive at least one document and to transmit the at least one document to a server computing device having at least one processor. The client computing device may be connected to one of a scanner and a facsimile device. The server computing device automatically matches the at least one document with a patient, indexes and classifies the at least one document, and sends the document to an electronic health record (EHR) system corresponding to a user of the client computing device.

According to one embodiment, a system includes one or more processors to receive a representation of a document from a client computing device, the document comprising one of a scanned document, a faxed document, and an electronic document, determine a document type of the document based at least on the representation of the document, index the document using a classification and index processing engine based on the document type, the document type comprising at least one of a plurality of document types used by an electronic health record (EHR) system, extract index data from the document based on the document type using the classification and index processing engine, and match the document with a patient from a database of the EHR system using the index data when the classification and index processing engine successfully indexes the document and extracts index data from the document.

According to a further embodiment, a method includes receiving, by at least one processor, a representation of a document from a client computing device, the document comprising one of a scanned document, a faxed document, and an electronic document, determining, by the at least one processor, a document type of the document based at least on the representation of the document, indexing, by the at least one processor, the document using a classification and index processing engine based on the document type, the document type comprising at least one of a plurality of document types used by an electronic health record (EHR) system, extracting, by the at least one processor, index data from the document using the classification and index processing engine, and matching, by the at least one processor, the document with a patient from a database of the EHR system using the index data when the classification and index processing engine successfully indexes the document and extracts index data from the document.

According to another embodiment, a non-transitory computer-readable medium includes instructions stored thereon that, when executed by one or more processors, cause the one or more processors to perform operations including receiving a representation of a document from a client computing device, the document comprising one of a scanned document, a faxed document, and an electronic document, determining a document type of the document based at least on the representation of the document, indexing the document using a classification and index processing engine based on the document type, the document type comprising at least one of a plurality of document types used by an electronic health record (EHR) system, extracting index data from the document using the classification and index processing engine, and matching the document with a patient from a database of the EHR system using the index data when the classification and index processing engine successfully indexes the document and extracts index data from the document.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

FIG. 7 shows index data extracted from a document being processed by the EHR indexing system according to an example embodiment.

FIG. 8 depicts a detailed view of a document being processed by the EHR indexing system according to an example embodiment.

FIG. 9 shows an exception management interface of the EHR indexing system according to an example embodiment.

DETAILED DESCRIPTION

Aspects of a system and method for electronic health record indexing provide a streamlined way for a healthcare organization to receive paper-based and electronic documents, classify and index the documents, and store a representation of the classified and indexed documents in a database associated with an electronic health record (EHR) system. The system and method disclosed herein operate with a variety of different EHR systems and provide a user with an easy-to-use web browser based interface. As an example, the system and method provided herein may act as middleware that allows a user to easily index and import documents into an EHR system.

Figure 1:
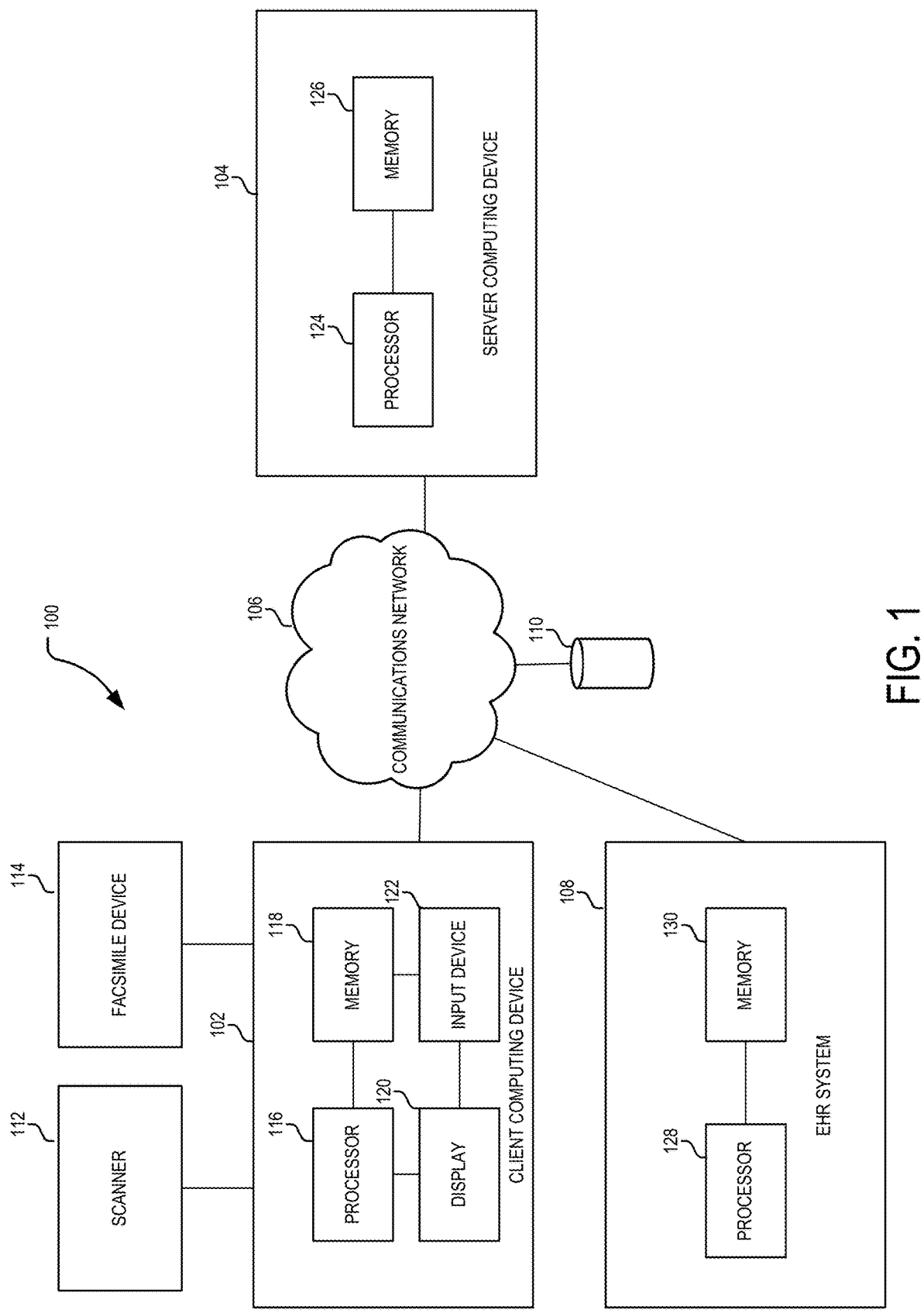
FIG. 1 is a block diagram of a computing system that includes an electronic healthcare record (EHR) indexing system according to an example embodiment.

FIG. 1 shows a block diagram of a computing system that includes an electronic healthcare record (EHR) indexing system 100. The EHR indexing system 100 includes one or more client computing devices 102 that are in communication with one or more server computing devices 104 via a communication network 106. The one or more client computing devices 102 may be in communication with an EHR system 108. One or more databases 110 may store electronic health record information associated with one or more users of the EHR indexing system 100 and one or more patients in one or more tables. The one or more client computing devices 102 may also be in communication with a scanner 112 and a facsimile device 114, among other devices.

As an example, the one or more computing devices communicate data in packets, messages, or other communications using a common protocol, e.g., Hypertext Transfer Protocol (HTTP) and/or Hypertext Transfer Protocol Secure (HTTPS). The one or more computing devices may communicate based on representational state transfer (REST) and/or Simple Object Access Protocol (SOAP). As an example, a first computer (e.g., the client computing device 102) may send a request message that is a REST and/or a SOAP request formatted using Javascript Object Notation (JSON) and/or Extensible Markup Language (XML). In response to the request message, a second computer (e.g., the server computing device 104) may transmit a REST and/or SOAP response formatted using JSON and/or XML.

The embodiments described herein may be based on Oauth, an open standard for authorization. Oauth allows producers of web services to grant third-party access to web resources without sharing usernames and/or passwords. In this case, the web resources may be the server computing device 104, the EHR system 108 and the database 110. As an example, the EHR system 108 and the database 110 may grant access to the server computing device 104. Oauth provides one application with one access token providing access to a subset of web resources on behalf of one user, similar to a valet key. In particular, the embodiments may be related to Oauth 2.0. While discussed in the context of Oauth, the present disclosure is not limited to Oauth.

The one or more server computing devices 104 are configured to receive data from and/or transmit data to the one or more client computing devices 102 through the communication network 106. Although the one or more server computing devices 104 are shown as a single server computing device, it is contemplated that the one or more server computing devices 104 may include multiple server computing devices, for example, in a cloud computing configuration. In addition, although the EHR system 108 is shown as separate from the client computing device 102 and the server computing device 104, it is contemplated that the EHR system 108 may be included in one of the client computing device 102 and the server computing device 104.

The communication network 106 can be the Internet, an intranet, or another wired or wireless communication network. For example, the communication network 106 may include a Mobile Communications (GSM) network, a code division multiple access (CDMA) network, $3^{rd}$ Generation Partnership Project (GPP), an Internet Protocol (IP) network, a wireless application protocol (WAP) network, a WiFi network, or an IEEE 802.11 standards network, as well as various combinations thereof. Other conventional and/or later developed wired and wireless networks may also be used.

According to an example embodiment, the one or more databases 110 may store electronic health record information associated with one or more users of the client computing device 102 in one or more tables. The electronic health record information may include user information (e.g., encrypted username information, password information, and/or token information for each user), document information including a record of each document received by the server computing device 104 that includes a unique document identifier for each document, classification information for each document and index information comprising one or more tags for each document, barcode information including a record of each barcode associated with the EHR indexing system 100, and mapping information for mapping each barcode to a particular document. The information may be stored in a structured query language (SQL) server database or another appropriate database management system within memory 126 and/or in the one or more databases 110. Additionally, the memory 126 and/or the databases 110 may also include a dedicated file server having one or more dedicated processors, random access memory (RAM), a Redundant Array of Inexpensive Disks (RAID) hard drive configuration, an Ethernet interface or other communication interface, and a server-based operating system.

The scanner 112 comprises scanning hardware, including a scanner, a multi-function device, or another type of hardware that can create a representative image of a paper document. In one embodiment, the scanning hardware may include a camera device for capturing the representative image of the paper document.

The representative image may be a 300 dpi (dots per inch) image. However, the representative image is not limited to being a 300 dpi image and the representative image may be a higher quality image or a lower quality image. In one example, the scanner includes a processor to process data, e.g., an image of a document, and memory to store data, e.g., the image of the document. The processor processes communications, builds communications, retrieves data from its memory, and stores data to its memory. The memory may include non-transitory memory, e.g., random access memory (RAM) and one or more hard disks. The non-transitory memory may include any tangible computer-readable medium including, for example, magnetic and/or optical disks, flash drives, and the like. The memory also may include volatile and/or non-volatile memory, e.g., a computer-readable storage medium such as a cache, random access memory (RAM), read only memory (ROM), flash memory, or other memory to store data and/or computer-readable executable instructions. In addition, the scanner 112 further includes at least one communications interface to transmit and receive communications, messages, and/or signals.

The facsimile device 114 comprises facsimile hardware, including a facsimile machine that can create a representative image of a paper document or electronic document and transmit the representative image of the paper document to another facsimile device or computing device. The facsimile device 114 also may receive a representative image of a paper document or electronic document via telephone transmission from another facsimile device or computing device. As an example, an original document is scanned with a first facsimile device and transmitted via telephone transmission to a second facsimile device, e.g., the facsimile device 114, which receives the telephone transmission. In one example, the facsimile device includes a processor to process data, e.g., an image of a document, and memory to store data, e.g., the image of the document. The processor processes communications, builds communications, retrieves data from its memory, and stores data to its memory. The memory may include non-transitory memory, e.g., random access memory (RAM) and one or more hard disks. The non-transitory memory may include any tangible computer-readable medium including, for example, magnetic and/or optical disks, flash drives, and the like. The memory also may include volatile and/or non-volatile memory, e.g., a computer-readable storage medium such as a cache, random access memory (RAM), read only memory (ROM), flash memory, or other memory to store data and/or computer-readable executable instructions. In addition, the facsimile device 114 further includes at least one communications interface to transmit and receive communications, messages, and/or signals.

The client computing device 102 includes one or more processors 116 to process data and memory 118 to store data. The one or more processors 116 may process machine/computer-readable executable instructions and data, and the memory 118 may store machine/computer-readable executable instructions and data including one or more applications, including a web browser. The processor 116 and memory 118 are hardware. The processor 116 processes communications, builds communications, retrieves data from its memory 118, and stores data to its memory 118. The memory 118 may include non-transitory memory, e.g., random access memory (RAM) and one or more hard disks. The non-transitory memory may include any tangible computer-readable medium including, for example, magnetic and/or optical disks, flash drives, and the like. The memory 118 also may include volatile and/or non-volatile memory, e.g., a computer-readable storage medium such as a cache, random access memory (RAM), read only memory (ROM), flash memory, or other memory to store data and/or computer-readable executable instructions. In addition, the at least one client computing device 102 further includes at least one communications interface to transmit and receive communications, messages, and/or signals.

The client computing device 102 can be a laptop computer, a personal digital assistant, a smartphone, a tablet computer, a standard personal computer, another processing device, or a dedicated electronic device having a processor and memory. The client computing device 102 may include a display 120, such as a computer monitor, for displaying data and/or graphical user interfaces. The display 120 can be a liquid-crystal display, a light-emitting diode display, an organic light-emitting diode display, a touch screen display, an e-ink display, an e-paper display, and other displays. The client computing device 102 may also include an input device 122, such as a keyboard or a pointing device (e.g., a mouse, trackball, pen, or touch screen) to enter data into or interact with graphical and/or other types of user interfaces.

The client computing device 102 may display on the display 120 a graphical user interface (or GUI) application, such as a browser application, to generate a graphical user interface on the display 120. The graphical user interface enables a user of the client computing device 102 to interact with the server computing device 104 and the EHR system 108.

The client computing device 102 uses the web browser to transmit messages and receive resources from the server computing device 104, the EHR system 108, and the database 110. The web browser provides a user interface to transmit a request to the server computing device 104 and receive a response from the server computing device 104.

In order to obtain access to protected resources associated with the server computing device 104 and/or the EHR system 108, e.g., resources stored in the database 110, the client computing device 102 may transmit a request including a representation of a username and a password to the server computing device 104 using lightweight directory access protocol (LDAP), HTTP, hypertext transport protocol secure (HTTPS) and/or other protocols. The request may be a LDAP request, a representational state transfer (REST) request, a Simple Object Access Protocol (SOAP) request, or another type of request. The server computing device 104 verifies the username and password and transmits a response to the client computing device 102. The server computing device 104 and/or the EHR system 108 may transmit an HTTP response, an HTTPS response, a LDAP response, a REST response, a SOAP response, and/or another type of response.

The username and password may be encrypted by the client computing device 102 using transport layer security (TLS), secure sockets layer (SSL), and/or other encryption protocols. The username and password may be encrypted using a cryptographic hash function (e.g., SHA-1, MD5, and others) to determine a hash-based message authentication code (HMAC) (hash-based message authentication code). In one example, "username.password" is encrypted using the cryptographic hash function. This cryptographic hash function allows the username and password to be verified and authenticated by the server computing device 104 without directly sending the username and password to the server computing device via the communications network 106.

The web browser may be a component of an application and/or service executable by the client computing device 102. For example, the web browser may be a single unit of deployable executable code. The web browser may be one application and/or a suite of applications. As an example, the web browser may be INTERNET EXPLORER®, SAFARI®, CHROME™, FIREFOX®, OPERA™, and other applications. The web browser may be part of another native application executed by the client computing device 102 (e.g., a web view within the native application) and/or the web browser may be a mobile web browser. According to an example embodiment, the web view may be embedded in a mobile application (e.g., an app) downloaded from a digital distribution application platform that allows users to browse and download applications developed with mobile software development kits (SDKs) including the App Store and GOOGLE PLAY® among others. The app may be installed on the client computing device, which may have an iOS operating system or an ANDROID™ operating system, among other operating systems. The web browser communicates messages to the server computing device 104 and receives messages from the server computing device 104, e.g., HTTP requests and corresponding HTTP responses. The responses may comprise requested content, including information associated electronic health record indexing.

The user of the client computing device 102 receives one or more barcodes from the server computing device 104. The barcodes may be presented as physical stickers each having a unique optical machine-readable representation of data and/or electronic data being a machine-readable representation of data affixed or attached to paper documents, fax documents, and electronic documents. The machine-readable representation of data, e.g., the barcode, corresponds to the document to which it is attached. The barcode may be a linear barcode, a two-dimensional matrix barcode, or another type of barcode.

The user of the client computing device 102 may transmit images of physical documents having physical stickers and not having physical stickers to the server computing device 104. Upon receipt by the server computing device 104, if the document does not have a physical sticker, the server computing device 104 may automatically affix or attach an electronic barcode to a representation of the document. In one example, the user of the client computing device 102 saves, e.g., drags and drops, documents and/or representations of documents into one or more folders locally in memory of the client computing device 102 and/or in other memory locations, e.g., a storage available via the communications network 106. The one or more folders may correspond with particular document attributes, e.g., barcodes, no barcodes, a particular medical division, a particular specialty, a particular physician, and other attributes. As an example, each folder may be designated for a particular type of document and/or a particular project corresponding to the EHR indexing system 100.

When the document is placed into the folder, a representation of the document is created by the server computing device 104 and/or the client computing device 102. The representation of the document includes an image of the document, e.g., a portable document format (PDF) of the document, a tagged image file format (TIF) of the document, or a Joint Photographic Experts Group (JPEG) of the document, and metadata that includes a folder identifier and a document identifier based on the folder, e.g., "Doctor-Brown" and "1234," among other information. The client computing device 102 and/or the server computing device 104 processes the document and performs document classification and indexing. The server computing device 104 classifies the document using the database 110 that includes representations of one or more types of documents and a document classification key for classifying the document and indexing the document based on the barcode, the representation of the document, and/or the metadata. Document indexing includes associating and/or tagging the document with one or more terms, e.g., unique patient number (e.g., medical record number), doctor name, procedure, date, and others. The server computing device 104 classifies the document by comparing the representation of the document with one or more master document representations in the database 110. The server computing device 104 stores the representation of the document, the metadata corresponding to the document, the classification information of the document, and the index information, among other information, in the database 110.

The one or more server computing devices 104 include one or more processors 124 to process data and memory 126 to store data. The one or more processors 124 may process machine/computer-readable executable instructions and data, and the memory 126 may store machine/computer-readable executable instructions and data including one or more applications, including an EHR indexing application for receiving one or more documents from users, classifying the one or more documents, indexing the one or more documents, and storing a representation of the one or more documents in the database 110. The processor 124 and memory 126 are hardware. The processor 124 processes communications, builds communications, retrieves data from its memory 126, and stores data to its memory 126. The memory 126 may include non-transitory memory, e.g., random access memory (RAM) and one or more hard disks. The non-transitory memory may include any tangible computer-readable medium including, for example, magnetic and/or optical disks, flash drives, and the like. The memory 124 also may include volatile and/or non-volatile memory, e.g., a computer-readable storage medium such as a cache, random access memory (RAM), read only memory (ROM), flash memory, or other memory to store data and/or computer-readable executable instructions. In addition, the at least one server computing device 104 further includes at least one communications interface to transmit and receive communications, messages, and/or signals.

The server computing device 104 can be a laptop computer, a personal digital assistant, a smartphone, a tablet computer, a standard personal computer, another processing device, or a dedicated electronic device having a processor 124 and memory 126. The EHR indexing application may be software as a service (SaaS) that is deployed to the server computing device 104 that is hosted and managed using MICROSOFT® AZURE™, Heroku, GOOGLE® App Engine, and Amazon Web Services, among others. The EHR system 108 includes one or more computing devices each having one or more processors 128 to process data and memory 130 to store data. The one or more processors 128 may process machine/computer-readable executable instructions and data, and the memory 130 may store machine/computer-readable executable instructions and data including one or more applications, including an EHR application for receiving data and information associated with documents received by the EHR indexing application of the server computing device 104. The processor 128 and memory 130 are hardware. The processor 128 processes communications, builds communications, retrieves data from its memory 130, and stores data to its memory 130. The memory 130 may include volatile and/or non-volatile memory, e.g., a computer-readable storage medium such as a cache, random access memory (RAM), read only memory (ROM), flash memory, or other memory to store data and/or computer-readable executable instructions such as data within database 110. In addition, the EHR system 108 further includes at least one communications interface to transmit and receive communications, messages, and/or signals.

The EHR application and EHR system 108 may be provided by Kronos, Midas, Lawson, Cerner, Siemens, Meditech, GE Healthcare, McKesson, and Epic, among others. Conventional EHR software applications lack advanced capture processing so the process to scan/import/index documents is tedious. The EHR application receives clinical data and representation of documents from the server computing device 104 and stores the clinical data and representation of documents with the electronic patient charts in the EHR system 108.

Figure 2:
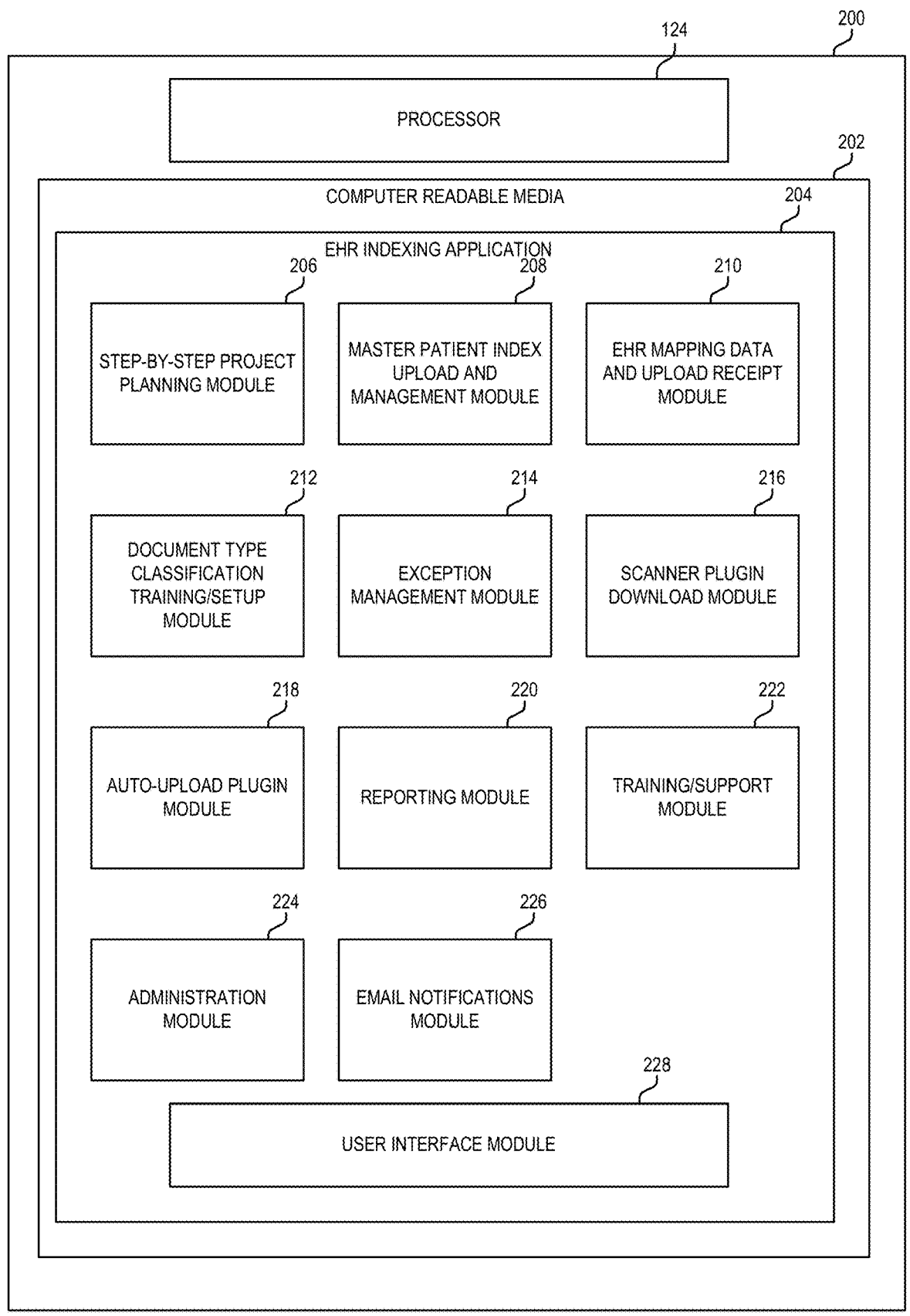
FIG. 2 is a block diagram of a server computing device of the EHR indexing system according to an example embodiment.

FIG. 2 shows a block diagram of the EHR indexing application of the server computing device 104 of the EHR indexing system 100 according to an example embodiment. The EHR indexing application also may be known as a classification and index processing engine that performs one or more optical character recognition algorithms on an incoming document to classify and index the document, and store a representation of the document. The server computing device 104 includes computer readable media (CRM) 202 on which the EHR indexing application 204 is stored. The computer readable media 202 may include volatile media, nonvolatile media, removable media, non-removable media, and/or another available medium that can be accessed by the processor 124. By way of example and not limitation, the computer readable media 202 comprises computer storage media and communication media. Computer storage media includes non-transitory memory, volatile media, nonvolatile media, removable media, and/or non-removable media implemented in a method or technology for storage of information, such as computer/machine-readable/executable instructions, data structures, program modules, or other data. Communication media may embody computer/machine-readable/executable instructions, data structures, program modules, or other data and include an information delivery media or system.

The EHR indexing application 204 includes a step-by-step project planning module 206, a master patient index upload and management module 208, an EHR mapping data and upload receipt module 210, a document type classification training/setup module 212, an exception management module 214, a scanner plugin download module 216, an auto-upload plugin module 218, a reporting module 220, a training/support module 222, an administration module 224, an email notifications module 226, and a user interface module 228, among other modules.

The step-by-step project planning module 206 allows a user of the client computing device 102 to track the progress of processing a single document and/or one or more documents and provides a progress indication or progress bar that visually depicts the status of a particular document and/or the one or more documents. The single document and/or one or more documents may be part of a "project." As an example, a project may include one or more documents to be processed for a particular healthcare facility, a particular EMR system, a particular day, and other possibilities. Each step associated with indexing the single document and/or the one or more documents is associated with a section of a progress bar. As an example, the progress bar shows a percentage to completion. The server computing device 104 transmits an indication of the progress bar to the client computing device 102.

The master patient index upload and management module 208 comprises a module for setting up recurring uploads of master patient index data used for processing the one or more documents. The master patient index data may be stored in the database 110 and may include patient demographic information for each patient including a patient name, a date of birth, a social security number or unique identification number, a medical record number, and other information. The list of terms may be updated by the user of the client computing device 102.

The EHR mapping data and upload receipt module 210 is a module that maps uploaded documents from the client computing device 102 to EHR document types and/or particular patients. The mapping may be a data structure that is generated and continually modified to correspond with one or more user assigned rules for classifying and indexing the document. The rules may include classification rules and indexing rules.

The EHR mapping data and upload receipt module 210 receives the document from the client computing device 102, classifies the document, indexes the document, stores a representation of the document in the memory 126 and/or the database 110, determines whether the representation of the document is validated or non-validated, and transmits the representation of the document to the EHR system 108 if the document is validated or forwards the representation of the document to the exception management module 214 if the document is non-validated.

According to an exemplary embodiment, the mapping data and upload receipt module 210 of the EHR indexing application 204 receives a document from the client computing device 102, classifies the document, and indexes the document based on the barcode affixed or attached to the document, the representation of the document and/or the metadata. The representation of the document may include a document layout, a location of data on the document, headers of the document, one or more logos on the document or embedded in the document, and anchor points of the document. The metadata may include data elements that reside on or within the document including patient demographic information, dates, physician information, and other healthcare data. In one example, the automatic classification and indexing of documents by the mapping data and upload receipt module 210 may be provided by READSOFT®. The mapping data and upload receipt module 210 of the EHR indexing application 204 determines whether the document is a validated document or a non-validated document. The mapping data and upload receipt module 210 transmits a representation of the validated document to the EHR system 108 and forwards the representation of the non-validated document to the exception management module 214.

As an example, the mapping data and upload receipt module 210 may determine a patient name, a unique medical record number of the document, a document type of the document, a document date of the document, a date of service of the document, and a provider name, among other information. This information may be determined by the mapping data and upload receipt module 210 based on the barcode and/or information stored in the database 110. Using the barcode, the representation of the document, and/or the metadata, the EHR indexing application 204 associates the document with a corresponding patient and indexes the document by tagging the document with one or more terms based on a document type, such as a lab result, correspondence, progress note, etc. The one or more terms may be based on the list of terms for indexing or tagging the documents. The EHR indexing application 204 captures relevant data from one or more data elements in the document including a date of service, a lab result, and other information. Additionally, the EHR application 204 optionally notifies another user of another client computing device 102 about further review of the document and/or sign-off.

The mapping data and upload receipt module 210 matches the document to a correct patient automatically, classifies the document type automatically, captures and indexes all relevant data available in the document using optical character recognition (OCR) software having an OCR engine, and automatically transmits the document or a reference to the document in the database 110 and associated relevant data to the EHR system 108 or transmits the document to the exception management module 214 for further review. In one example, the optical character recognition software may be provided by READS OFT®. OCR comprises performing pattern recognition based on one or more alphabet sets, and converting scanned or photographed images of a page of typewritten, handwritten, or printed text into machine-readable characters that the server computing device 104 can search or index.

The document type classification training/setup module 212 is a module for setting up one or more classifications and indexes for forms and data elements. The document type classification training/setup module 212 receives one or more master uploaded documents and requests information associated with the one or more uploaded documents from the user of the client computing device 102 and/or the EHR system 108. In one example, each of the one or more documents may be a type of document that is unknown to the document type classification training/setup module 212. The document type classification training/setup module 212 requests setup information from the user of the client computing device 102 including information about the type of document that is unknown to the document type classification training/setup module 212 and stores the setup information in the memory 126 and/or the database 110.

The exception management module 214 is a module for managing documents that the EHR indexing application 204 could not classify and/or index. The exception management module 214 may include a submodule that resides in the EHR system 108. The exception management module 214 collects additional exception user input from a user of the client computing device 102 when the EHR indexing application is unable to obtain data elements from a document. The exception management module 214 transmits a representation of the document and information that was captured from the document to the client computing device 102 and requests that the user of the client computing device 102 provide the document with a classification and/or missing information. The client computing device 102 transmits user assigned classification and/or the missing information to the exception management module 214 and the exception management module 214 releases the completed document and transmits the representation of the completed document, the user assigned classification, and/or the missing information to the EHR system 108.

The scanner plugin download module 216 receives a request from the client computing device 102 for a scanner plugin application and transmits the scanner plugin application to the client computing device 102. The scanner plugin application may be installed in memory 118 of the client computing device 102. The scanner plugin application receives data from the scanner 112 when a particular document is scanned. The data includes a representation of the document, e.g., a PDF of the document. The scanner plugin application automatically uploads the representation of the document to the EHR indexing application 204 and the EHR mapping data and receipt module 210 processes the representation of the document. This scanner plugin application is compatible with most standard scanners and includes an installation wizard, test functionality, and scanning functionality. In one example, the scanner plugin application may be provided by DELL®. The scanner plugin application may provide automatic blank page removal, deskew, image cleanup, automatic rotation, multiple format image output, basic indexing, multiple clots per inch (DPI) settings, and other scanner plugin functionality.

The auto-upload plugin module 218 receives a request from the client computing device 102 for an auto-upload plugin application and transmits the auto-upload plugin application to the client computing device 102. The auto-upload plugin application installs on the client computing device 102 and receives one or more electronic files from a user of the client computing device 102 that may be dropped into a particular folder associated with the auto-upload plugin application. Any documents dropped into folder will be automatically uploaded by the client computing device 102 to the server computing device 104. The server computing device 104 receives the documents, performs the automatic classification and indexing of documents by the mapping data and upload receipt module 210, and forwards the documents to the EHR system 108.

The auto-upload plugin application may be installed in memory 118 of the client computing device 102. The auto-upload plugin application receives a document from the user of the client computing device 102 and generates a representation of the document, e.g., a PDF of the document. The auto-upload plugin application automatically uploads the representation of the document to the EHR indexing application 204, the EHR mapping data and receipt module 210 processes the representation of the document, and forwards the documents to the EHR system 108. The auto-upload plugin application assists with placing the document into the corresponding patient record, labeling the document by document type, and including any additional index data captured by EHR indexing application 204. This auto-upload plugin application includes an installation wizard, test functionality, and upload functionality. In one example, the auto-upload plugin application may be provided by NEXTGEN®.

The reporting module 220 is a module for providing indexing statistics and metrics to the user of the client computing device 102. The reporting module 220 generates one or more reports for the user of the client computing device 102 including information provided by the EHR indexing application 204 and transmits the one or more reports to the client computing device 102. The reports may include information about documents processed by the EHR indexing application 204 filtered by project, document type, date, number of documents, number of pages, physician code, commonly used forms, user data, location, and other relevant data. A report may be a PDF providing the information that is attached to an email sent to the client computing device 102. In another example, the report may be a web-based report and a reference to the report, e.g., a uniform resource locator (URL), may be transmitted to the client computing device 102.

The training module 222 receives a request from the user of the client computing device 102 for training information and transmits the training information to the client computing device 102. The training information may include step by step indexing documentation, videos, frequently asked questions, realtime chat and phone support information.

The administration module 224 is a module for managing one or more users associated with the EHR indexing application 204 and managing account information. Managing one or more users includes managing security rights, managing access to the EHR indexing application 204, managing administration rights, managing usernames and passwords, managing user groups, and managing user contact information associated with the EHR indexing application 204. Managing account information includes managing a name associated with an account, managing contact information associated with an account, managing billing information associated with an account, and managing add-on options associated with an account.

The email notifications module 226 is a module for setting up, editing, and deleting e-mail alerts to users defined using the administration module 224 for items such as exception management, forms management, report availability, and completion of processing by the EHR indexing application 204. As an example, an email notification may be sent to an email address when an exception occurs, when a particular number of documents are in the exception queue, when new report is available, and when a project is completed, among others. More particularly, an email notification may be sent to an email address when a particular document may be converted to an electronic form for future automation, an email notification may be sent to an email address when a report from the EHR indexing application 204 is available to view, and an email notification may be sent to an email address when a batch of documents has been processed and completed by the EHR indexing application 204.

The user interface module 228 generates resources associated with a user interface of the EHR indexing application 204. The user interface module 228 may generate resources for a native and/or web-based graphical user interface (GUI) that accepts input and provides output. The user interface module 228 receives a request for the resources associated with the user interface from the client computing device 102 and transmits the resources associated with the user interface to the client computing device 102. The user interface module 228 may send data to other modules of the EHR indexing application 204 and receive data from other modules of the EHR indexing application 204.

Figure 3:
FIG. 3 illustrates a screenshot of a user interface of the EHR indexing system according to an example embodiment.

FIG. 3 shows a screenshot 300 of an exemplary user interface of the EHR indexing application 204 displayed by the client computing device 102 according to an example embodiment. The exemplary user interface may be displayed on a display 120 of the at least one client computing device 102 and may be a web-based interface. As shown in FIG. 3, the user interface includes a setup tab, an exceptions tab (which is shown in FIG. 3), an administration tab, and a support tab. As shown in FIG. 3, the user of the at least one client computer 102 is presented with a list of document exceptions by the exception management module 214 including Exception 1— Document 14, Exception 2— Document 16, Exception 3— Document 20, and Exception 4— Document 21. For each of the exceptions, the user of the client computing device 102 may enter additional information to address the exception. The exception management module 214 receives the additional information and determines whether the additional information eliminates the exception. If the additional information eliminates the exception, the exception management module transmits the representation of the document to the EHR system 108. The user interface also includes a chat interface provided by the training module 222 used to interact with administrators of the at least one server computing device 104.

Figure 4:
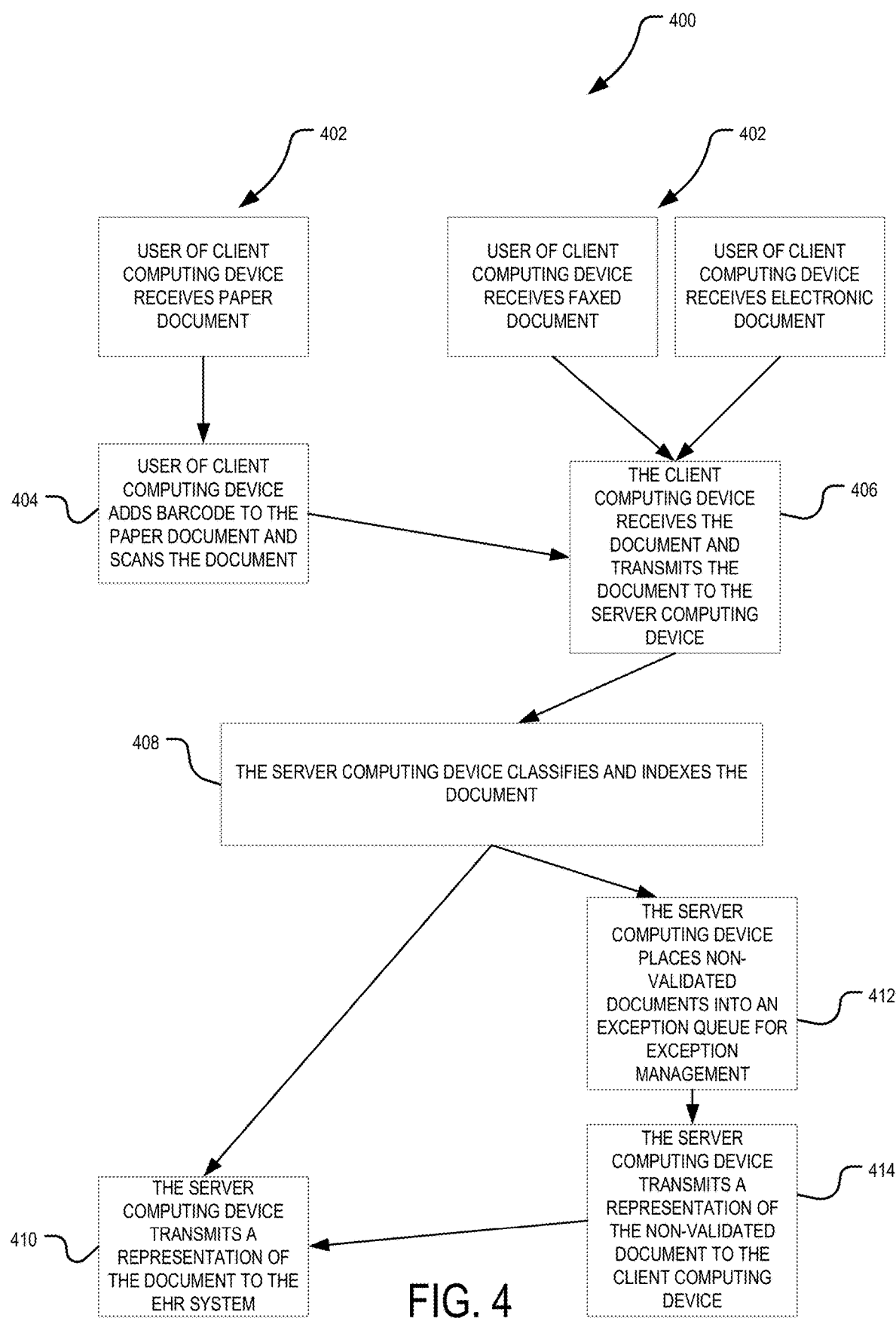
FIG. 4 shows a flowchart of a method for processing a document by the EHR indexing system according to an example embodiment.

FIG. 4 shows a flowchart 400 of a method for processing one or more documents by the EHR indexing system 100 according to an example embodiment. The document may be one of a paper document, a faxed document, and an electronic document. In step 402, a user of the client computing device 102 receives the document. The document may be a paper document to be scanned by the scanner 112, a faxed document received by the facsimile device 114, or an electronic document. In step 404, the user of the client computing device 102 adds a barcode to the paper document and scans the document using the scanner 112. The barcode may be a physical proprietary barcode. In step 406, the client computing device 102 receives a representation of the scanned document, the faxed document, or the electronic document. The scanned document, the faxed document or the electronic document may be imported by one of the scanner 112 and the facsimile device 114 and may be delivered to a folder stored in memory of the client computing device 102 using one of the scanner plugin and the auto-upload plugin. The client computing device 102 transmits/uploads the document to the at least one server 104 for classification and index processing.

In step 408, the EHR mapping data and upload receipt module 210 of the server computing device 104 executes classification and index processing by automatically classifying and indexing the document. If the processing is successful and the document is validated, in step 410, the at least one server computing device 104 transmits a representation of a completed document or a reference to the representation of the completed document to the EHR system 108 and the representation of the completed document may be stored in database 110. However, if the method is not successful, in step 412, the exception management module 214 of the server computing device 104 places non-validated documents into an exception queue for exception management. The exception management module 214 transmits a representation of the document and information that was captured from the document to the client computing device 102 and requests that the user of the client computing device 102 provide the document with a classification and/or missing information.

In step 414, the user of the client computing device 102 may visually review and manage document exceptions using the web browser. The client computing device 102 transmits the missing information to the exception management module 214 and the exception management module 214 releases the completed document to the EHR system 108. Once the document exceptions are managed by the user, the server computing device 104 transmits a representation of a completed document to the EHR system 108 and the representation of the completed document may be stored in database 110.

Figure 5:
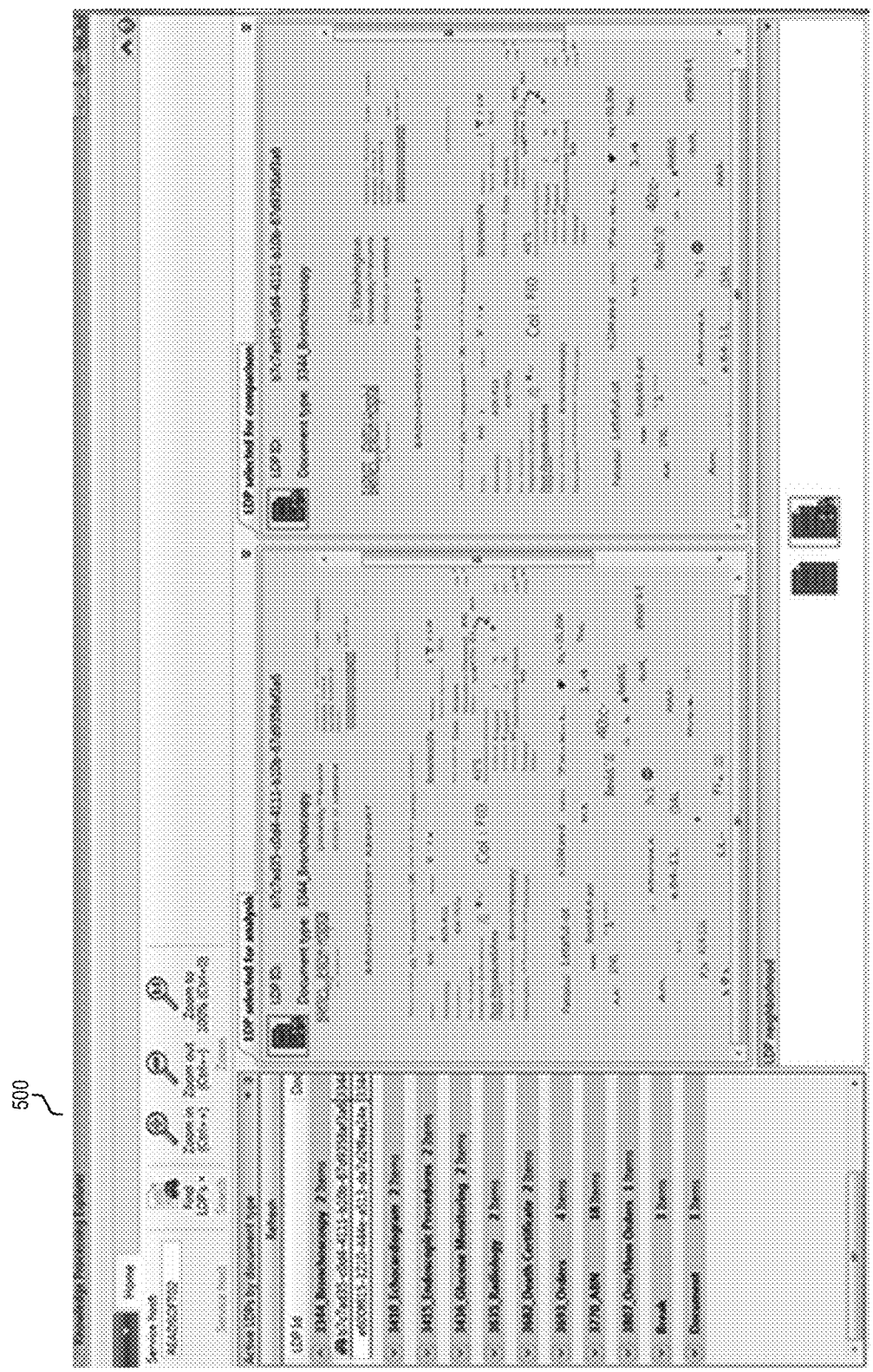
FIG. 5 shows a document being processed by the EHR indexing system according to an example embodiment.

FIG. 5 shows a document 500 being processed by the EHR indexing application 204 of the EHR indexing system 100 according to an example embodiment. As an example, the left pane of the user interface shown in FIG. 5 represents a document being processed and the right pane of the user interface shown in FIG. 5 represents a master document for comparison with the document being processed. In this example, the document is a bronchoscopy report document.

The bronchoscopy report document is automatically classified by the EHR indexing application 204 as a bronchoscopy document. Information captured from the document shown in the left pane is compared with the information in the document shown in the right pane to determine that this document is a bronchoscopy document. The document shown in the right pane is the master bronchoscopy document stored in the database 110 and used to compare to any new documents received by the server computing device 104. The EHR indexing application 204 of the server computing device 104 compares the incoming document with one or more master documents and if possible, assigns the incoming document a classification, and indexes the incoming document by tagging the document with one or more terms captured from the document or based on the barcode affixed or attached to the document. If the EHR indexing application 204 is unable to classify the incoming document and/or index the incoming document, the EHR indexing application 204 places a representation of the incoming document into the exception queue for processing.

Figure 6:
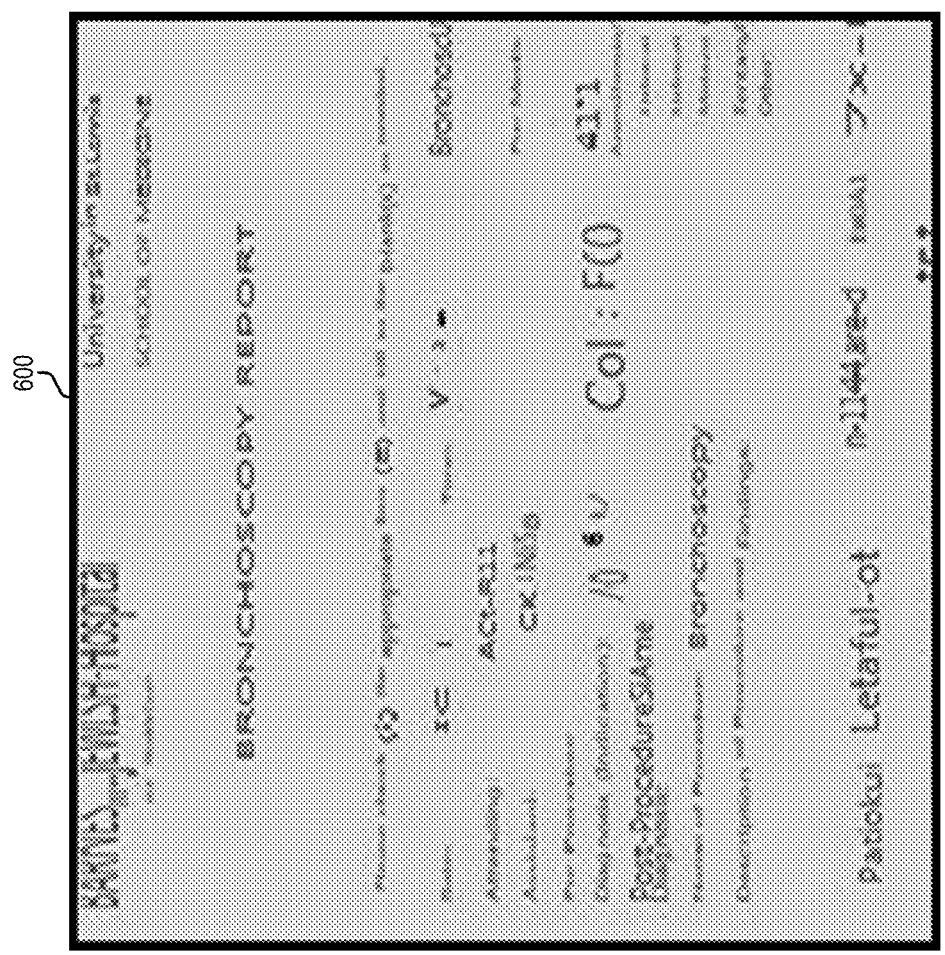
FIG. 6 depicts a detailed view of a document being processed by the EHR indexing system according to an example embodiment.

FIG. 6 depicts a detailed view of a document 600 being processed by the EHR indexing application 204 of the EHR indexing system 100 according to an example embodiment. In this example, the document 600 is a bronchoscopy document and is a portion of the document being processed shown in FIG. 5.

Figure 7:
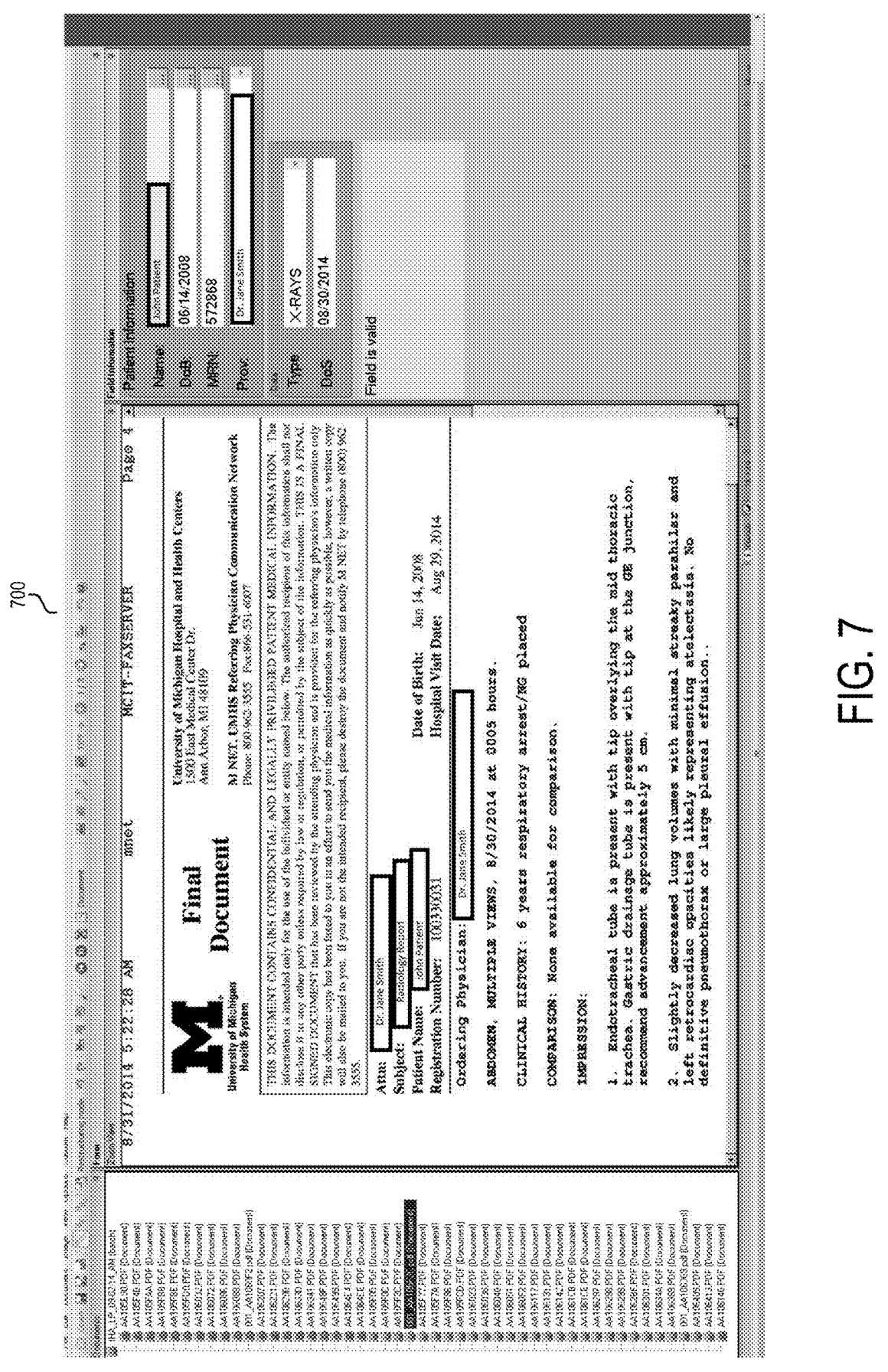

FIG. 7 shows index data extracted from a document 700 being processed by the EHR indexing application 204 of the EHR indexing system 100 according to an example embodiment. FIG. 7 shows a view of index data extracted from the document 700 using OCR. The index data includes patient information and other data extracted by the EHR indexing application 204 that populates the fields including Type (e.g., classification)— X-RAYS, Name, DoB (date of birth), MRN (medical record number), provider, (Prov.), DoS (date of service), and other information. FIG. 7 shows a user interface provided by the web browser that a user of the client computing device 102 can use to visually inspect and confirm data elements and index data captured by the EHR indexing application 204.

FIG. 8 depicts a detailed view of a document 800 being processed by the EHR indexing application 204 of the EHR indexing system 100 according to an example embodiment. As shown in FIG. 8, a physical document includes a plurality of text boxes comprising user interface elements that may be used to modify the text in the document. Each user interface element is an editable user interface element that receives input from the user of the client computing device 102 using the input device 122, e.g., a keyboard and/or mouse. The user may view and modify the editable user interface element in the event that the EHR indexing application 204 incorrectly or accurately performs OCR on the text in the document.

Figure 9:
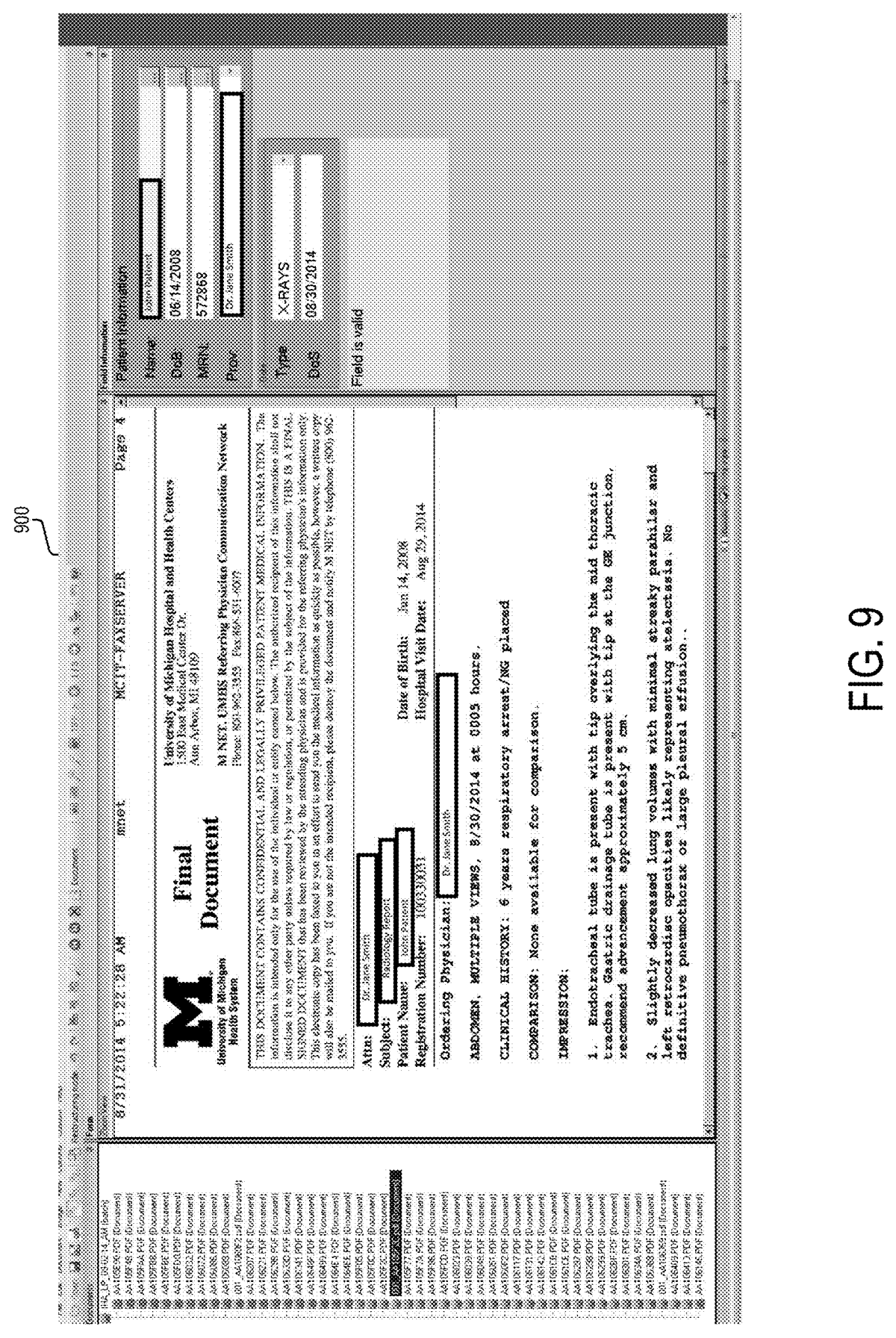

FIG. 9 shows an exception management interface 900 of the EHR indexing application 204 of the EHR indexing system 100 according to an example embodiment. The exception management interface 900 is provided jointly by the exception management module 214 and the user interface module 228 of the EHR indexing application 204. The EHR indexing application 204 populates the fields including Type—X-RAYS, Name, DoB (date of birth), MRN (medical record number), provider, (Prov.), DoS (date of service), and other information. The exception management interface 900 allows the user of the client computing device 102 to view and modify each of the fields that are editable user interface elements. After the user of the client computing device 102 has completed editing the representation of the document and/or adding information, the server computing device 104 stores the representation of the document, classification, and the indexing information in the database 110 and transmits the representation of the document and/or a reference to the representation of the document to the EHR system 108.

Figure 10:
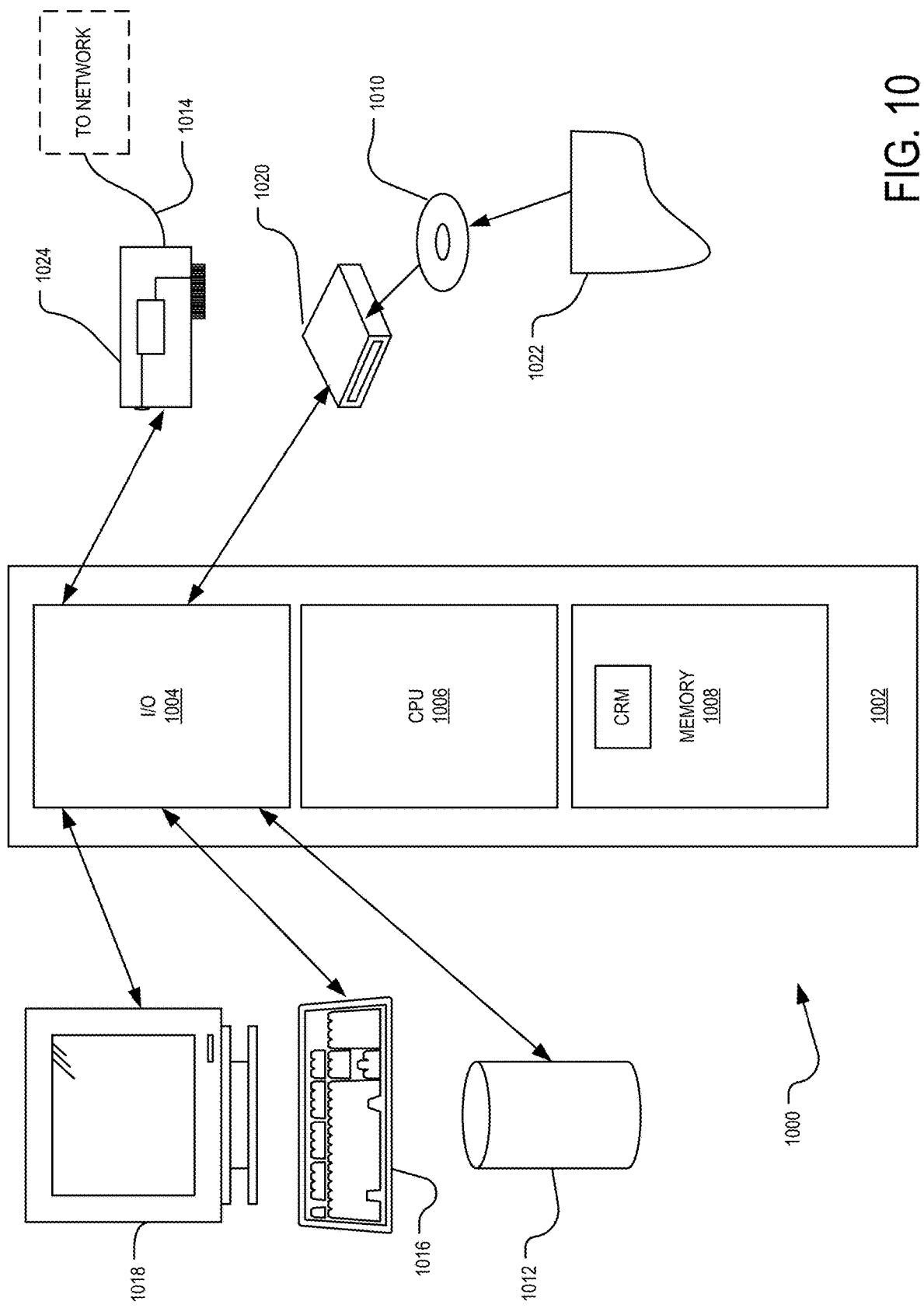
FIG. 10 illustrates a block diagram of an example computer device for use with the example embodiments.

The EHR indexing application 204 uses the information received from the user of the client computing device 102 to retrain and teach the EHR indexing application 204. When performing OCR on future documents, the EHR indexing application 204 may more accurately predict and/or determine characters found in paper documents, faxed documents, and/or electronic documents. Thus, the EHR indexing application 204 is able to learn new information based on input from the user of the client computing device 102. In other words, the EHR indexing application may modify, create, or delete rules used by the EHR mapping data and upload receipt module 210 that map input text to output machine-readable text. FIG. 10 illustrates an example computing system 1000 that may implement various systems, such as the client computing device 102, the server computing device 104, and the EHR system 108, and methods discussed herein, such as process 400. A general purpose computer system 1000 is capable of executing a computer program product to execute a computer process. Data and program files may be input to the computer system 1000, which reads the files and executes the programs therein such as the web browser and the EHR indexing application 204. Some of the elements of a general purpose computer system 1000 are shown in FIG. 10 wherein a processor 1002 is shown having an input/output (I/O) section 1004, a central processing unit (CPU) 1006, and a memory section 1008. There may be one or more processors 1002, such that the processor 1002 of the computer system 1000 comprises a single central-processing unit 1006, or a plurality of processing units, commonly referred to as a parallel processing environment. The computer system 1000 may be a conventional computer, a server, a distributed computer, or any other type of computer, such as one or more external computers made available via a cloud computing architecture. The presently described technology is optionally implemented in software devices loaded in memory 1008, stored on a configured DVD/CD-ROM 1010 or storage unit 1012, and/or communicated via a wired or wireless network link 1014, thereby transforming the computer system 1000 in FIG. 10 to a special purpose machine for implementing the described operations.

The memory section 1008 may be volatile media, non-volatile media, removable media, non-removable media, and/or other media or mediums that can be accessed by a general purpose or special purpose computing device. For example, the memory section 1008 may include non-transitory computer storage media and communication media. Non-transitory computer storage media further may include volatile, nonvolatile, removable, and/or non-removable media implemented in a method or technology for the storage (and retrieval) of information, such as computer/machine-readable/executable instructions, data and data structures, engines, program modules, and/or other data. Communication media may, for example, embody computer/machine-readable/executable, data structures, program modules, algorithms, and/or other data. The communication media may also include an information delivery technology. The communication media may include wired and/or wireless connections and technologies and be used to transmit and/or receive wired and/or wireless communications.

The I/O section 1004 is connected to one or more user-interface devices (e.g., a keyboard 1016 and a display unit 1018), a disc storage unit 1012, and a disc drive unit 1020. Generally, the disc drive unit 1020 is a DVD/CD-ROM drive unit capable of reading the DVD/CD-ROM medium 1010, which typically contains programs and data 1022. Computer program products containing mechanisms to effectuate the systems and methods in accordance with the presently described technology may reside in the memory section 1004, on a disc storage unit 1012, on the DVD/CD-ROM medium 1010 of the computer system 1000, or on external storage devices made available via a cloud computing architecture with such computer program products, including one or more database management products, web server products, application server products, and/or other additional software components. Alternatively, a disc drive unit 1020 may be replaced or supplemented by a floppy drive unit, a tape drive unit, or other storage medium drive unit. The network adapter 1024 is capable of connecting the computer system 1000 to a network via the network link 1014, through which the computer system can receive instructions and data. Examples of such systems include personal computers, Intel or PowerPC-based computing systems, AMD-based computing systems, ARM-based computing systems, and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 1000 is connected (by wired connection and/or wirelessly) to a local network through the network interface or adapter 1024, which is one type of communications device. When used in a WAN-networking environment, the computer system 1000 typically includes a modem, a network adapter, or any other type of communications device for establishing communications over the wide area network. In a networked environment, program modules depicted relative to the computer system 1000 or portions thereof, may be stored in a remote memory storage device. It is appreciated that the network connections shown are examples of communications devices for and other means of establishing a communications link between the computers may be used.

In an example implementation, source code executed by the client computing device, the server computing device 104, and the EHR system 108, a plurality of internal and external databases including the database 110, source databases, and/or cached data on servers are stored in memory 118 of the client computing device 102, memory 126 of the server computing device 104, memory 130 of the EHR system 108, or other storage systems, such as the disk storage unit 1012 or the DVD/CD-ROM medium 1010, and/or other external storage devices made available and accessible via a network architecture. The source code executed by the client computing device 102, the server computing device 104, and the EHR system 108 may be embodied by instructions stored on such storage systems and executed by the processor 1002.

Some or all of the operations described herein may be performed by the processor 1002, which is hardware. Further, local computing systems, remote data sources and/or services, and other associated logic represent firmware, hardware, and/or software configured to control operations of the EHR indexing system 100 and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 1002 and a user may interact with a Graphical User Interface (GUI) using one or more user-interface devices (e.g., the keyboard 1016, the display unit 1018, and the user devices 1004) with some of the data in use directly coming from online sources and data stores. The system set forth in FIG. 10 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon executable instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A system, comprising:
   at least one processor to:
   transmit at least one barcode to a client computing device;
   receive a representation of a document from the client computing device, the document comprising one of a scanned document, a faxed document, and an electronic document;
   determine a document type of the document based on one of the at least one barcode and the representation of the document;
   index the document using a classification and index processing engine based on the document type, the document type comprising at least one of a plurality of document types used by an electronic health record (EHR) system;
   extract index data from the document based on the document type using the classification and index processing engine; and
   match the document with a patient from a database of the EHR system using the index data when the classification and index processing engine successfully indexes the document and extracts index data from the document.

2. The system of claim 1, wherein the at least one barcode comprises a unique optical machine-readable representation of data.

3. The system of claim 1, wherein the at least one barcode comprises one of a linear barcode and a two-dimensional matrix barcode.

4. The system of claim 1, wherein the at least one barcode is affixed to a paper document and scanned by a scanner to generate the scanned document.

5. The system of claim 1, wherein the at least one barcode comprises a sticker affixed to a paper document and is scanned by a scanner to generate the scanned document.

6. The system of claim 1, wherein the at least one barcode is an electronic barcode added to the representation of the document.

7. The system of claim 1, wherein the at least one barcode is affixed to a paper document and sent via facsimile hardware that generates the faxed document.

8. The system of claim 1, wherein the at least one barcode comprises a sticker affixed to a paper document and is sent via facsimile hardware that generates the faxed document.

9. The system of claim 1, the at least one processor further to determine that the representation of the document does not have the at least one barcode and automatically attach the at least one barcode to the representation of the document.

10. A method, comprising:
    transmitting, by at least one processor, at least one barcode to a client computing device;
    receiving, by the at least one processor, a representation of a document from the client computing device, the document comprising one of a scanned document, a faxed document, and an electronic document;
    determining, by the at least one processor, a document type of the document based on one of the at least one barcode and the representation of the document;
    indexing, by the at least one processor, the document using a classification and index processing engine based on the document type, the document type comprising at least one of a plurality of document types used by an electronic health record (EHR) system;
    extracting, by the at least one processor, index data from the document based on the document type using the classification and index processing engine; and
    matching, by the at least one processor, the document with a patient from a database of the EHR system using the index data when the classification and index processing engine successfully indexes the document and extracts index data from the document.

11. The method of claim 10, wherein the at least one barcode comprises a unique optical machine-readable representation of data.

12. The method of claim 10, wherein the at least one barcode comprises one of a linear barcode and a two-dimensional matrix barcode.

13. The method of claim 10, wherein the at least one barcode is affixed to a paper document and scanned by a scanner to generate the scanned document.

14. The method of claim 10, wherein the at least one barcode comprises a sticker affixed to a paper document and is scanned by a scanner to generate the scanned document.

15. The method of claim 10, wherein the at least one barcode is an electronic barcode added to the representation of the document.

16. The method of claim 10, wherein the at least one barcode is affixed to a paper document and sent via facsimile hardware that generates the faxed document.

17. The method of claim 10, wherein the at least one barcode comprises a sticker affixed to a paper document and is sent via facsimile hardware that generates the faxed document.

18. The method of claim 10, further comprising determining that the representation of the document does not have the at least one barcode and automatically attaching the at least one barcode to the representation of the document.

19. A non-transitory computer-readable medium having instructions stored thereon that, when executed by at least one processor, cause the at least one processor to perform operations comprising:
    transmitting at least one barcode to a client computing device;
    receiving a representation of a document from the client computing device, the document comprising one of a scanned document, a faxed document, and an electronic document;
    determining a document type of the document based on one of the at least one barcode and the representation of the document;
    indexing the document using a classification and index processing engine based on the document type, the document type comprising at least one of a plurality of document types used by an electronic health record (EHR) system;
    extracting index data from the document based on the document type using the classification and index processing engine; and
    matching the document with a patient from a database of the EHR system using the index data when the classification and index processing engine successfully indexes the document and extracts index data from the document.

20. The non-transitory computer-readable medium of claim 19, wherein the at least one barcode comprises a unique optical machine-readable representation of data.

* * * * *